(12) United States Patent
Gray et al.

(10) Patent No.: US 10,251,666 B2
(45) Date of Patent: Apr. 9, 2019

(54) ENDOSCOPIC MUCOSAL RESECTION SINGLE STEP HOOD

(71) Applicant: Boston Scientific Scimed, Inc., Maple Grove, MN (US)

(72) Inventors: Jeff Gray, Sudbury, MA (US); Samuel Raybin, Marlborough, MA (US); Kevin Scott Gell, Roxbury Crossing, MA (US); Paul Smith, Smithfield, RI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 89 days.

(21) Appl. No.: 15/159,213

(22) Filed: May 19, 2016

(65) Prior Publication Data

US 2016/0338723 A1 Nov. 24, 2016

Related U.S. Application Data

(60) Provisional application No. 62/164,313, filed on May 20, 2015.

(51) Int. Cl.
| | | |
|---|---|---|
| *A61B 1/00* | (2006.01) | |
| *A61B 17/3205* | (2006.01) | |
| *A61B 17/00* | (2006.01) | |
| *A61B 17/32* | (2006.01) | |
| *A61B 18/12* | (2006.01) | |

(Continued)

(52) U.S. Cl.
CPC .... *A61B 17/32056* (2013.01); *A61B 1/00089* (2013.01); *A61B 17/00234* (2013.01); *A61B 17/320016* (2013.01); *A61B 18/12* (2013.01); *A61B 18/1492* (2013.01); *A61B 2017/00269* (2013.01); *A61B 2017/306* (2013.01); *A61B 2018/00077* (2013.01); *A61B 2018/00291* (2013.01); *A61B 2018/00482* (2013.01); *A61B 2018/00595* (2013.01); *A61B 2018/00601* (2013.01); *A61B 2018/00982* (2013.01); *A61B 2018/141* (2013.01); *A61B 2018/144* (2013.01);

(Continued)

(58) Field of Classification Search
CPC .............. A61B 1/0008; A61B 1/00087; A61B 1/00089; A61B 17/32056; A61B 17/320016
USPC ................... 600/127, 129; 606/113–114, 170
See application file for complete search history.

(56) References Cited

U.S. PATENT DOCUMENTS

| | | | |
|---|---|---|---|
| 5,897,487 A | 4/1999 | Ouchi | |
| 5,968,056 A * | 10/1999 | Chu | A61B 17/12013 606/139 |

(Continued)

FOREIGN PATENT DOCUMENTS

JP 2010-022697 A 2/2010

OTHER PUBLICATIONS

International Search Report and Written Opinion for corresponding Application No. PCT/US2016/033282 dated Aug. 3, 2016, (10 pages).

*Primary Examiner* — Matthew J Kasztejna
(74) *Attorney, Agent, or Firm* — Bookoff McAndrews, PLLC

(57) ABSTRACT

The present disclosure provides systems and methods for cutting mucosal tissue. In particular, the present disclosure provides an endoscopic hood with an integrated wire for single-step tissue cutting. The endoscopic hood is particularly useful for performing repeated cutting, for example EMR resections, without the need for assistance by a nurse or medical technician.

17 Claims, 6 Drawing Sheets

(51) Int. Cl.
 *A61B 18/00* (2006.01)
 *A61B 18/14* (2006.01)
 *A61B 17/30* (2006.01)

(52) U.S. Cl.
 CPC ... *A61B 2217/005* (2013.01); *A61B 2218/002* (2013.01)

(56) References Cited

U.S. PATENT DOCUMENTS

| | | | | |
|---|---|---|---|---|
| 6,306,081 | B1* | 10/2001 | Ishikawa | A61B 1/00082 600/115 |
| 6,689,051 | B2* | 2/2004 | Nakada | A61B 1/00089 600/129 |
| 7,122,002 | B2* | 10/2006 | Okada | A61B 1/00087 600/127 |
| 7,588,580 | B2* | 9/2009 | Okada | A61B 1/00087 600/104 |
| 9,155,554 | B2* | 10/2015 | Smith | A61B 17/320016 |
| 9,456,811 | B2* | 10/2016 | Sibbitt, Jr. | A61B 17/0057 |
| 2008/0125782 | A1* | 5/2008 | Rydell | A61B 17/32056 606/79 |
| 2013/0158546 | A1 | 6/2013 | Toomey et al. | |
| 2013/0172918 | A1 | 7/2013 | Smith et al. | |

\* cited by examiner

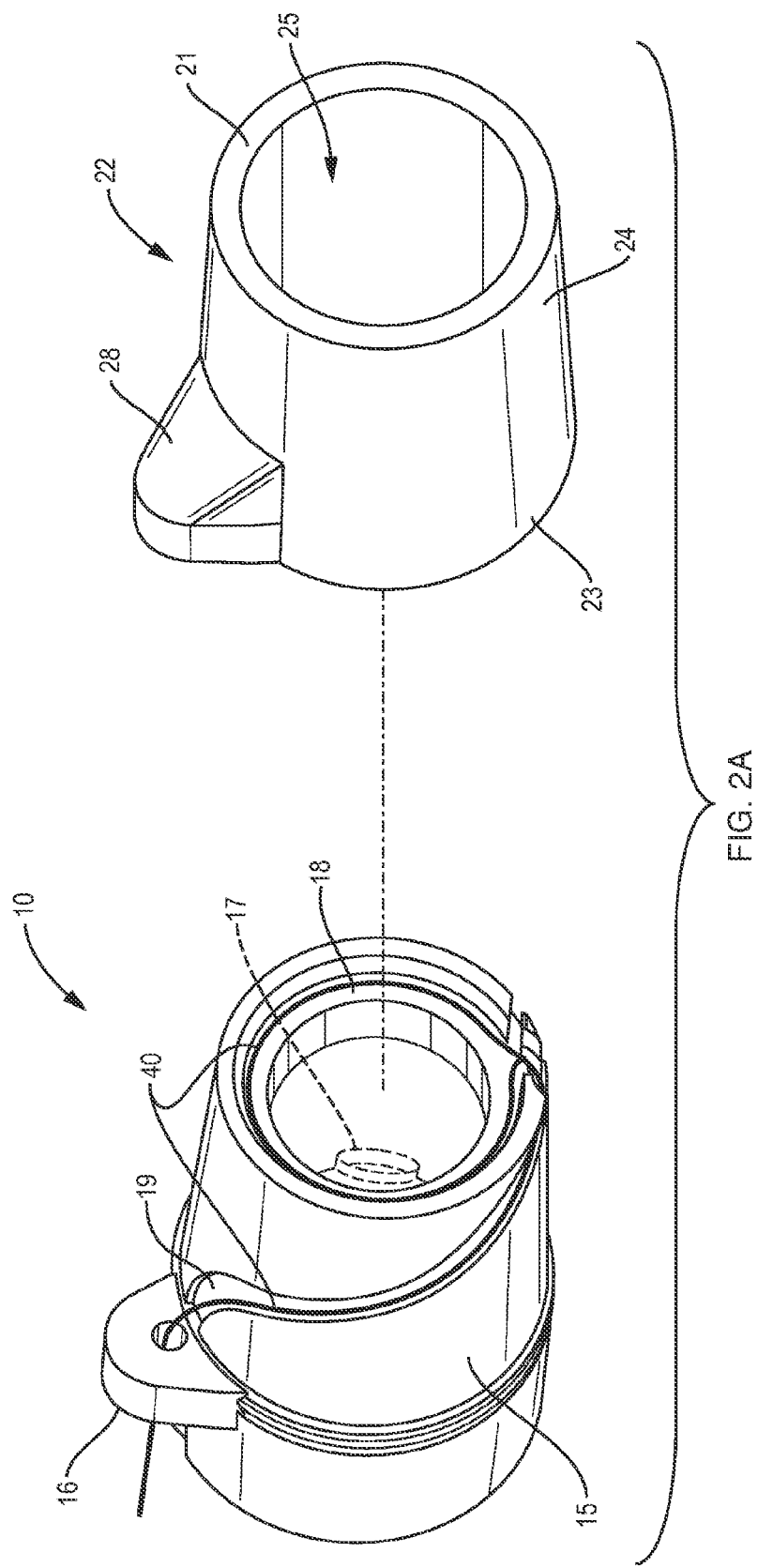

ENDOSCOPIC MUCOSAL RESECTION SINGLE STEP HOOD

CROSS-REFERENCE TO RELATED APPLICATIONS

This application claims the benefit of U.S. Provisional Application No. 62/164,313, filed May 20, 2015, the disclosure of which is incorporated herein by reference in its entirety.

TECHNICAL FIELD

The present disclosure relates to the field of endoscopy. Specifically, the present disclosure relates to systems and methods for cutting, for example resecting and/or dissecting, abnormal or diseased mucosal tissue. More specifically, the present disclosure relates to an endoscopic hood designed to create and cut a pseudo-polyp in a single step.

BACKGROUND

Organ walls are composed of several layers: the mucosa (surface layer), the submucosa, the muscularis (muscle layer) and the serosa (connective tissue layer). A variety of lesions comprising dead, diseased or abnormal tissue may form on the mucosal walls of the colon, esophagus, stomach and duodenum. For example, gastrointestinal, colonic and esophageal cancers may form within the mucosal layer and manifest as a polyp or tissue mass that extends into the lumen of the respective organ.

Endoscopic mucosal resection (EMR) is a minimally invasive technique by which cancerous or otherwise abnormal tissues are resected without disrupting the integrity of the organ wall. EMR is generally performed using an endoscope that includes a long narrow tube equipped with a light, video camera and one or more channels to receive a variety of medical instruments. During an EMR procedure, the endoscope is passed down the esophagus or guided through the rectum to the site of a cancerous or abnormal tissue within the mucosal wall of the target organ. The distal end of the endoscope is equipped with an endoscopic hood that is positioned over the tissue to be resected. Once properly positioned, suction is applied to the endoscope to draw the target tissue into the endoscopic hood, where it is then resected using a variety of techniques known in the art. The excised tissue is then extracted from the endoscope for examination and/or disposal.

Currently available EMR systems use suction to draw the target tissue into the endoscopic hood and deploy an elastic band around the base of the resulting pseudo-polyp. The suction is then released and the EMR hood and endoscope are pulled proximally to free the pseudo-polyp. A resection snare is passed through the working channel of the endoscope and manipulated to capture and resect the pseudo-polyp from the surrounding tissue. Once freed, the resected tissue is recaptured within the EMR hood using suction, or by introducing a separate grasping element (i.e., basket, forceps etc.) through the endoscope working channel. As multiple elastic bands are provided with such devices, several resections may be performed using the same EMR hood.

Other EMR systems do not require elastic bands to create the pseudo-polyp. Instead, a snare is deployed around the inside of the EMR hood so that the tissue can be resected immediately following formation of the pseudo-polyp. A major drawback of this system, however, is the minimal recovery afforded by the snare once the resection has been performed. This requires a new snare to be inserted and deployed within the EMR hood for each subsequent tissue resection.

Although the EMR systems described above use different techniques to form and resect the pseudo-polyp, they are similar in that both require multiple users to simultaneously control the endoscope and resection snare. In a typical EMR procedure the endoscope is controlled/maneuvered by a physician while the snaring/resecting steps are performed by a nurse. For example, when the physician has determined that the target tissue is properly positioned within the EMR hood, he/she must instruct the nurse to tighten the snare around the pseudo-polyp, followed by an instruction to apply cauterization energy. Once the target tissue is fully resected, the physician then instructs the nurse to cease cauterization and retract the snare. As one might expect, this process limits the physician's tactile sense for the procedure and requires a significant amount of communication with the nurse. This disclosure is related to an EMR hood that allows the physician to create and resect a pseudo-polyp in a single step without the need for additional assistance.

SUMMARY

Particular aspects of the disclosure are described in the Summary and Detailed Description, below. Although the disclosure has been described in connection with specific aspects, it should be understood that the disclosure as claimed should not be unduly limited to such specific aspects.

In one aspect, the present disclosure relates to an endoscopic hood configured to be disposed at a distal end of an endoscope. The endoscopic hood includes a proximal portion, a distal portion, a lumen extending between the proximal and distal portions, a wire track disposed about an inner circumference of the distal portion, and a wire channel extending between the proximal and distal portions. The wire channel is in communication with the wire track. For example, the wire channel and the wire track may merge with each other at a gradual angle such that the wire channel and wire track can receive a wire. The wire channel may extend along an inner wall of the endoscopic hood. Alternatively, the wire channel may extend along an outer wall of the endoscopic hood. The wire track may include a planar surface that is substantially perpendicular to the inner wall of the endoscopic hood. The wire track may be formed as a groove disposed within the inner wall of the endoscopic hood. An anchoring element may be positioned adjacent to the site at which the wire channel merges with the wire track. An end of the wire may be secured (i.e., tied, anchored, welded etc.) to the anchoring element. The anchoring element may also include an opening or aperture to slidably receive a portion of the wire. An elastomeric sleeve may be configured to form an interference fit with the outer surface of the endoscopic hood. The elastomeric sleeve may include a distal cap that is coextensive with and substantially parallel to the wire track. The elastomeric sleeve may enclose the wire channel that extends along the outer wall of the endoscopic hood. An endoscope may be attached to the proximal portion of the endoscopic hood. The endoscope may include at least one working channel in communication with the lumen of the endoscopic hood.

In another aspect, the present disclosure relates to a tissue cutting system including an endoscope, an endoscopic hood coupled to the distal end of the endoscope, an actuation handle coupled to the proximal end of the elongate member and a wire that forms a loop about the wire track and extends proximally along the wire channel to the actuation handle. The endoscope includes a proximal end, a distal end and a lumen extending therebetween. The endoscopic hood includes a proximal portion, a distal portion and a lumen extending between the proximal and distal portions. A wire track is disposed about an inner circumference of the distal portion of the endoscopic hood. A wire channel extends between the proximal and distal portions of the endoscopic hood, and is in communication with the wire track. The wire channel and wire track are configured to receive a wire. A protective elongate member may enclose at least a portion of the wire extends along the length of the endoscope between the endoscopic hood and the actuation handle. The protective elongate member may extend along the exterior surface of the endoscope. Alternatively, the protective elongate member may extend along the lumen of the endoscope. A portion of the wire may be configured to move from an open-loop configuration to a closed-loop configuration. For example, retracting the actuation handle may move a portion of the wire into a closed loop configuration and advancing the actuation handle may move a portion of the wire into an open-loop configuration.

In yet another aspect, the present disclosure relates to a method of cutting tissue, including inserting, into a body lumen of a patient, a medical device comprising an endoscope, an endoscopic hood coupled to the distal end of the endoscope, an actuation handle coupled to the proximal end of the elongate member and a wire that forms a loop about the wire track and extends proximally along the wire channel to the actuation handle. The endoscope includes a proximal end, a distal end and a lumen extending therebetween. The endoscopic hood includes a proximal portion, a distal portion and a lumen extending between the proximal and distal portions. A wire track is disposed about an inner circumference of the distal portion of the endoscopic hood. A wire channel extends between the proximal and distal portions of the endoscopic hood, and is in communication with the wire track. The wire channel and wire track are configured to receive a wire. The endoscopic hood is positioned over the surface of the target tissue. Once properly positioned, the target tissue is drawn into the lumen of the endoscopic hood. The wire is then moved into a closed-loop configuration around the tissue. Cauterization energy is then applied to the wire to cut the tissue. Once the tissue has been cut, the wire is returned to an open-loop configuration. Fluid may be injected in or around the target tissue before the target tissue is drawn into the lumen of the endoscopic hood. The endoscopic hood may be repositioned over the surface of a second target tissue after the first target tissue has been cut. These steps may be repeated as necessary to remove multiple target tissues.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures:

FIG. 2A is a side view of an outer sleeve configured to slide over the endoscopic hood, according to an embodiment of the present disclosure.

It is noted that the drawings are intended to depict only typical or exemplary embodiments of the disclosure. It is further noted that the drawings may not be necessarily to scale. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one or ordinary skill in the art to which the disclosure belongs. Finally, although embodiments of the present disclosure are described with specific reference to systems and method for cutting mucosal tissue using an endoscope, it should be appreciated that the endoscopic hood of the present disclosure may be applicable to cutting a variety of tissues using a variety of introduction devices, sheaths or systems, such as trocars, catheters, laparoscopes, colonoscopes, ureteroscopes and the like. As used herein, the term "distal" refers to the end farthest away from a medical professional when introducing a device into a patient, while the term "proximal" refers to the end closest to the medical professional when introducing a device into a patient. As used herein, the term "cutting" may include any suitable type of cutting, including resection performed as part of an endoscopic mucosal resection procedure. In some instances, the terms "cutting" and "resection" may be used interchangeably. It should be understood, however, that aspects of the disclosure may also be applicable to other types of cutting, such as dissection as part of an endoscopic submucosal dissection procedure.

Figure 1A:
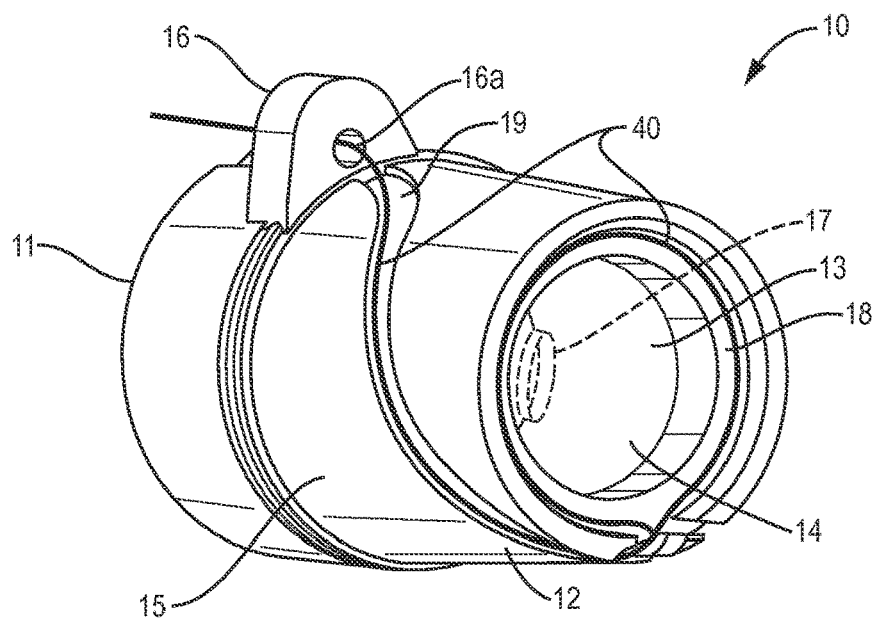
FIG. 1A is a side perspective view of an endoscopic hood, according to an embodiment of the present disclosure.

FIG. 1A depicts an endoscopic hood 10 according to one embodiment of the present disclosure. The endoscopic hood 10 is preferably substantially cylindrical and optionally includes a proximal portion 11, a distal portion 12 and a lumen 13 (i.e., working channel) extending therebetween. The lumen 13 is defined by an inner wall 14 with a preferably substantially constant inner diameter. The endoscopic hood further may include an outer wall 15 with a preferably varying (e.g., tapered) outer diameter. The distal portion 12 is configured to permit tissue to be drawn into the lumen 13 of the endoscopic hood 10 using endoscopic suction. A substantially circular resection wire track 18 may be disposed about an inner circumference of the inner wall 14 at the distal portion 12 of the endoscopic hood 10. The resection wire track 18 preferably includes a planar surface that is preferably substantially perpendicular to the inner wall 14 of the endoscopic hood 10. The resection wire track 18 may be in communication with a resection wire channel 19 that preferably extends along the outer wall 15 of the endoscopic hood 10 between the proximal 11 and distal 12 portions. The resection wire track 18 and resection wire channel 19 are preferably configured to receive at least a portion of a resection wire 40.

The resection wire 40 is comprised of an electrically conductive material with sufficient flexibility that it slides freely along the resection wire track 18, resection wire channel 19 and protective elongate member 29 (FIG. 3) without kinking, bending or otherwise developing sites of fatigue. In one embodiment, the resection wire 40 includes a diameter of at least 0.25 mm, more preferably at least 0.50 mm and even more preferably at least 1.00 mm to provide sufficient stiffness (i.e., pushability) along its entire length such that advancing one end of the resection wire causes the opposite end of the resection wire to advance without any portion of the resection wire bending or kinking.

Materials suitable for use as a resection wire include electrically conductive metals or alloys selected, for example, from platinum group metals, particularly platinum, rhodium, palladium, and rhenium, as well as tungsten, gold, silver, tantalum, and alloys of these metals including platinum/tungsten alloys and nickel-titanium alloys (nitinol) among others. The resection wire may be formed from a monofilament material (e.g., monofilament nitinol) or a braided material as are known in the art. In one embodiment, the ability of the resection wire 40 to repeatedly move between an open-loop configuration and closed-loop configuration may be further enhanced by heat treating and/or mechanically shaping a distal portion of the resection wire such that it assumes the shape of the resection wire track 18 and/or resection wire channel 19 when in the relaxed/unconstrained configuration.

Figure 1B:
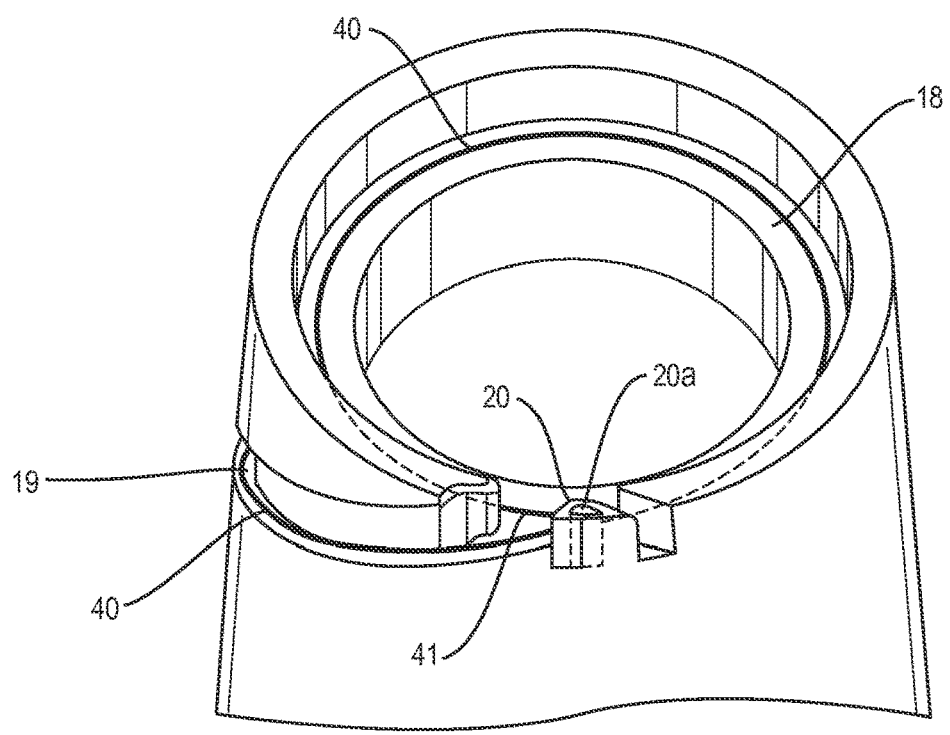
FIG. 1B is a top perspective view of the endoscopic hood of FIG. 1A.
Figure 3:
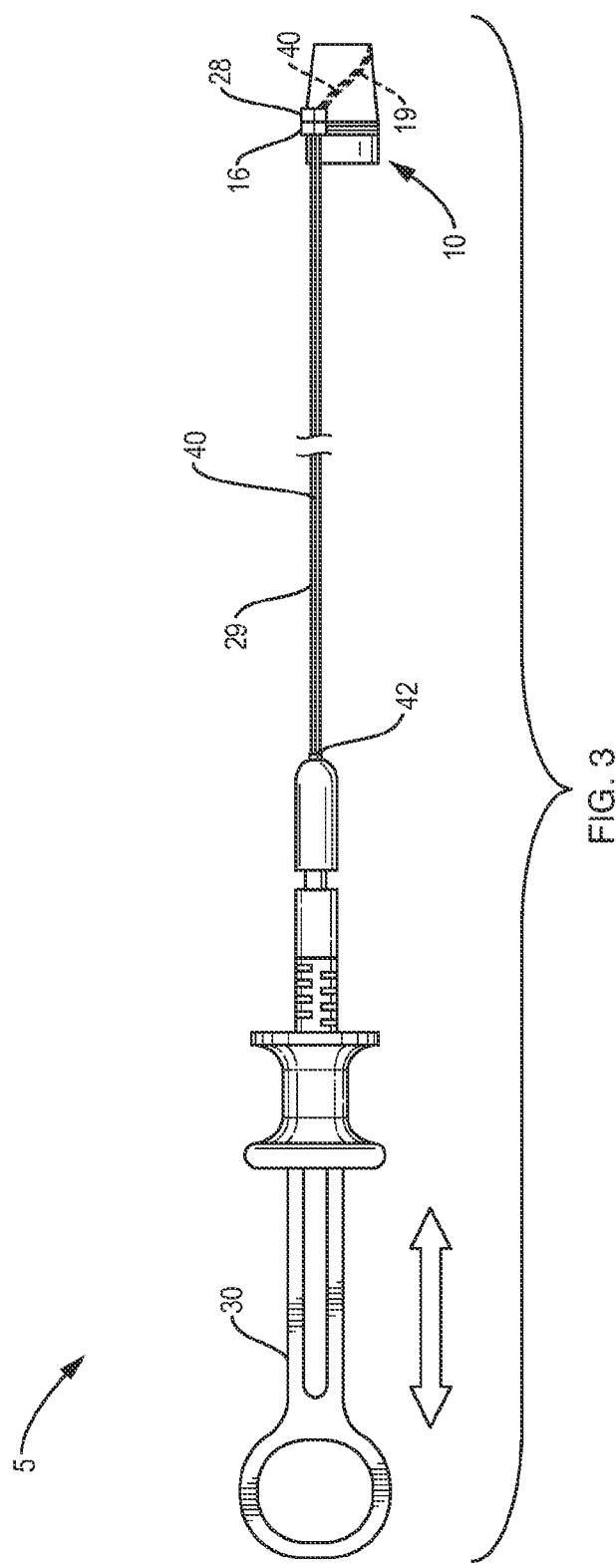
FIG. 3 is a side view of the endoscopic hood and outer sleeve of FIG. 2B connected to an actuation handle by a protective elongate member, according to an embodiment of the present disclosure.

In the open-loop configuration, the resection wire 40 is secured to a distal portion of the endoscopic hood 10, travels around the planar surface of the resection wire track 18 to form a loop, and continues proximally along the resection wire channel 19 through a protective elongate member 29 to an actuation handle 30 (see FIG. 3). As best shown in FIG. 1B, a first end 41 of the resection wire 40 is secured to an anchoring element 20 positioned adjacent to the site at which the resection wire track 18 and resection wire channel 19 merge. The anchoring element 20 includes an aperture 20a through which the resection wire 40 passes as it proceeds from the resection wire track 18 to the resection wire channel 19. The gradual angle at which the resection wire track 18 and resection wire channel 19 merge/intersect allows the resection wire 40 to smoothly transition between an open-loop configuration and closed-loop configuration as the actuation handle is extended and retracted, respectively. Referring again to FIG. 1A, the outer wall 15 of the proximal portion 11 of the endoscopic hood 10 further includes an outwardly extending tab 16 with an opening 16a therethrough. The tab 16 serves as an attachment point for a protective elongate member 29 that connects the endoscopic hood 10 to the actuation handle 30 (as shown in FIG. 3). The resection wire 40 passes through the opening 16a of the outwardly extending tab 16 and extends through the protective elongate member 29 to the actuation handle 30.

Still referring to FIG. 1A, the outer wall 15 of endoscopic hood 10 includes a generally decreasing taper from the proximal portion 11 to distal portion 12 to allow the endoscopic hood to navigate body passageways in a minimally invasive manner. As shown in FIG. 2A, an outer sleeve 22 is configured to slide over the outer wall 15 of the endoscopic hood 10 to fully enclose the resection wire channel 19. The outer sleeve 22 includes a proximal portion 23, a distal portion 24 and a lumen 25 extending therebetween. The lumen 25 of the outer sleeve 22 is defined by an inner wall with a varying diameter that corresponds to the taper of the outer wall 15 of the endoscopic hood. The inner diameter of the lumen 25 is undersized as compared to the corresponding outer wall of the endoscopic hood. The outer sleeve 22 is comprised of a sufficiently elastomeric material, including, but not limited to, rubber or silicone, such that it expands when positioned over the endoscopic hood, thereby forming an interference fit with the underlying endoscopic hood. The outer sleeve 22 further includes a raised portion 28 that presses against the tab 16 and guides the resection wire into the opening 16a of tab 16.

Figure 2B:
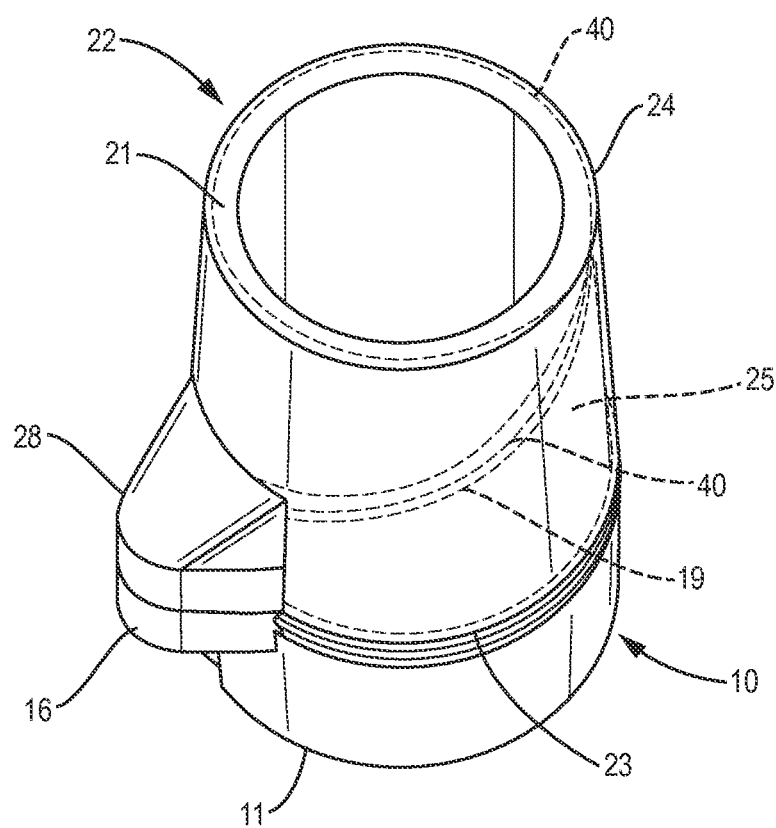
FIG. 2B is a top perspective view of the outer sleeve of FIG. 2A forming an interference fit with the endoscopic hood, according to an embodiment of the present disclosure.
Figure 4A:
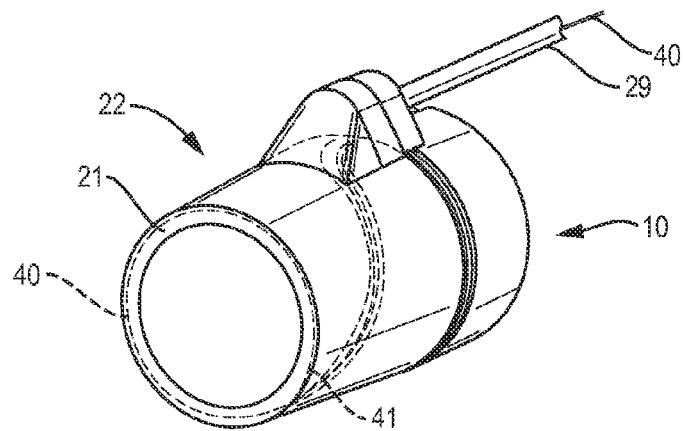
FIG. 4A is a side perspective view of the resection wire in an open-loop configuration when the actuation handle of FIG. 3 is in the extended configuration.
Figure 4B:
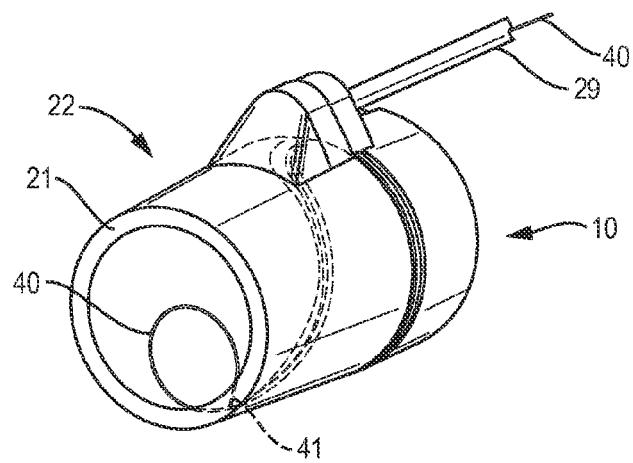
FIG. 4B is a side perspective view of the resection wire in a partially closed-loop configuration when the actuation handle of FIG. 3 is in the retracted configuration.

Still referring to FIG. 2A, the distal end of the sleeve 22 also includes an inwardly projecting cap 21 that is coextensive with, and substantially parallel to, the resection wire track 18. As best shown in FIG. 2B, when the sleeve 22 is positioned over the endoscopic hood 10, the cap 21 covers, but does not contact, the resection wire track 18 to form a groove within which the resection wire 40 lies. Enclosing the resection wire channel 19 with the outer sleeve 22 prevents the resection wire 40 from jumping out of the resection wire channel 19 as the actuation handle (not shown) is extended or retracted. Similarly, partially enclosing the resection wire track 18 with the cap 21 ensures that repeated movement of the resection wire between the open-loop configuration and closed-loop configuration occurs in a plane perpendicular to the lumen 13 of the endoscopic hood 10 (see FIGS. 4A-B).

Figure 4C:
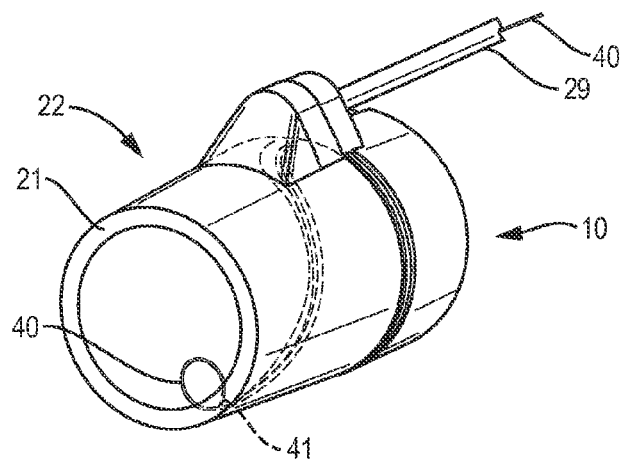
FIG. 4C is a side perspective view of the resection wire in a closed-loop configuration when the actuation handle of FIG. 3 is in the retracted configuration.

Referring to FIG. 3, the tab 16 serves as an attachment point for a protective elongate member 29 that extends between the endoscopic hood 10 and the actuation handle 30. A portion of the resection wire 40 passes through the opening 16a of the tab 16 and through the lumen of the protective elongate member 29 to the actuation handle 30. The second end 42 of the resection wire 40 is secured to the actuation handle 30 such that the resection wire 40 moves between an open-loop configuration (FIG. 4A) and a closed-loop configuration (FIGS. 4B-C) as the actuation handle 30 is extended and retracted, respectively. In one embodiment, the protective elongate member 29 may be configured to travel through a working channel of the endoscope (not shown). In another embodiment, the protective elongate member 29 may extend along an exterior surface of the endoscope, thereby providing more room within the endoscope working channel for the introduction of additional medical instruments.

Figure 5A:
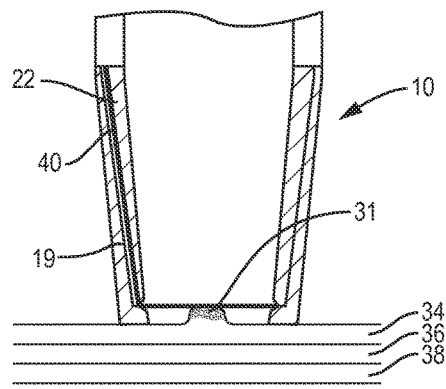
FIGS. 5A-5F depict the steps involved in resecting a target mucosal tissue using a single step endoscopic hood, in accordance with an embodiment of the present disclosure.
Figure 5B:
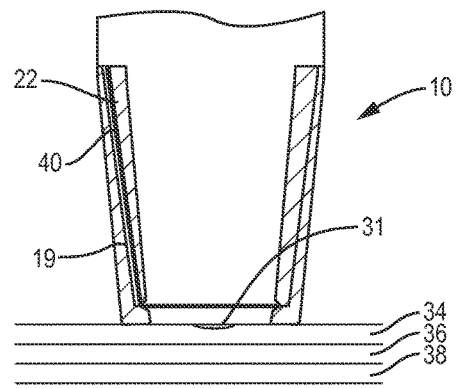

As will be understood by one of skill in the art, the depth of the cut made by the resecting wire loop is critical. If the cut is too deep the muscularis layer may be injured, possibly leading to a perforation. Conversely, a cut that is too shallow may not remove all of the affected tissue, such that additional procedures are required or, worse, contributing to the development of metastatic cancer. Typically, more than 2.0 mm of target tissue clearance is required to assure complete removal. FIGS. 5A-5F illustrate the use of the endoscopic hood 10 in performing an EMR procedure. As shown, a physician may introduce the endoscopic hood 10 attached to the distal end of an endoscope (not shown) into a patient's body through a natural anatomical opening or an incision. Referring to FIGS. 5A-B, the distal portion 12 of the endoscopic hood 10 is positioned over and in contact with the mucosal layer 34 of the target tissue 31. As depicted in FIG. 5A, the target tissue 31 (shaded area) may include a raised region or polyp that extends outward from the mucosal surface. Polyps, such as pedunculated polyps, may be characterized by a stalk attached to the mucosal layer. Such polyps are easily drawn into the endoscopic hood with relatively little suction. Alternatively, as depicted in FIG. 5B, the target tissue may lie substantially flat, or only slightly raised, along the mucosal layer 34 of the target tissue. For example, certain other polyps, such as sessile polyps, may exhibit a broad base that is devoid of any stalk portion such that they lay substantially flat on the mucosal surface. Such polyps are often difficult to grasp without applying an amount of suction that draws in part of the underlying muscularis layer.

In one embodiment, a fluid such as a gel, saline solution, hypertonic glucose, indigo carmine, ethylene blue or the like is injected beneath the target tissue to form a bleb, thereby raising the target tissue. The raised tissue can then be drawn into the endoscopic hood for resection. In some instances, the target tissue may be too large to remove in a single step, and must be removed by segmental resection, in which repeated fluid injections and subsequent tissue removal are performed along the entire length of the affected area.

Figure 5C:
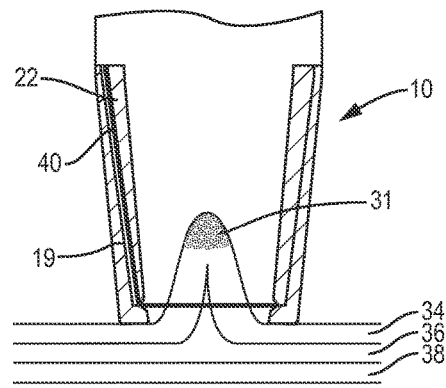

Referring to FIG. 5C, once the endoscope is properly positioned, the physician applies vacuum suction to draw the mucosal layer 34 of the target tissue (and a portion of surrounding healthy tissue) into the lumen 13 of the endoscopic hood 10. In one embodiment, the vacuum suction is provided through the endoscope (i.e., endoscope suction). In another embodiment, the vacuum source is provided through the protective elongate member 29. In yet another embodiment, the vacuum suction is provided by a separate tube running through the working channel of the endoscope or along an outer surface of the endoscope.

Figure 5D:
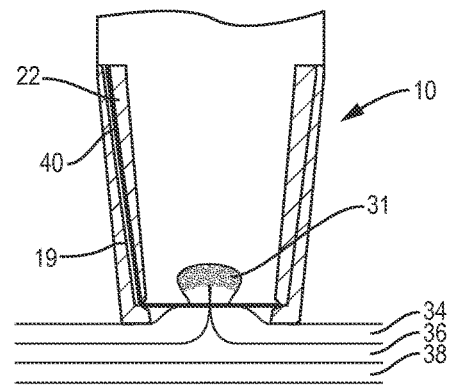
Figure 5E:
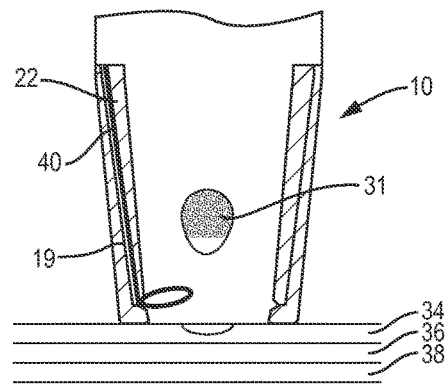

Referring to FIG. 5D, with the vacuum source maintaining the target tissue within the lumen 13 of the endoscopic hood 10, the physician retracts the actuation handle 30 such that the resection wire 40 disposed about the resection wire track 18 in an open-loop configuration moves towards a closed-loop configuration to tighten around the outer surface of the target tissue. Once the physician determines that the resection wire 40 has sufficiently tightened around the target tissue, cauterization energy is applied to the resection wire from an energy source (not shown) to cauterize the tissue. As shown in FIG. 5E, the cauterization energy applied to the tightened loop 33 of the resection wire 40 is sufficient to resect (i.e. cut) the target tissue free from the mucosal layer 34 without cutting either the submucosa 36 or muscularis 38 layers. In the event that the target tissue is not released by the first application of cauterization energy, the physician may further retract the actuation handle 30 such that the resection wire 40 further tightens around the target tissue, followed by a second application of cauterization energy. These steps may be repeated as necessary to cut the target tissue free from the mucosal layer. Alternatively, the physician may apply cauterization energy while the actuation handle 30 is being retracted such that the target tissue is cut as the resection wire 40 moves into an increasingly small closed-loop configuration. It should be appreciated that the cauterization energy applied to the resection wire 40 creates a cauterization zone that extends beyond the diameter of the resection wire. This allows the resection wire 40 to cut entirely through the target tissue without necessarily having to move the resection wire into its smallest possible closed-loop configuration. The ability to simultaneously control the actuation handle 30 and the 13 application of cauterization energy allows the physician to resect tissues with a greater level of precision than can be achieved using conventional EMR systems that require multiple users. Moreover, the greater dexterity afforded by the single step endoscopic hood 10 allows the physician to stop retracting the actuation handle 30 as soon as the tissue is fully resected. This further enhances the ability to perform multiple/consecutive tissue resections by allowing the resection wire 40 to avoid unnecessarily small closed-loop configurations, thereby minimizing the stress exerted upon the resection wire 40 and the distance required to return to resection wire track 18.

Figure 5F:
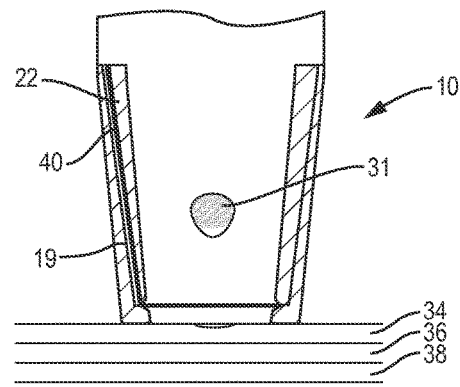

Referring to FIG. 5F, once the target tissue is released from the mucosal layer, the physician may advance the actuation handle 30 such that the resection wire 40 returns to the open-loop configuration disposed within the resection wire track 18. Once the vacuum suction has been removed, the physician may withdraw the endoscope from the patient. Alternatively, the physician may reposition the distal portion 12 of the endoscopic hood 10 over and in contact with the mucosal surface 34 of another target tissue, which is then resected by repeating the steps outlined above.

Although the endoscopic hood 10 and outer sleeve 22 described herein are provided as separate pieces that interlock to form an interference fit that encloses the resection wire track 18 and resection wire channel 19, the endoscopic hood 10 may also be formed as a single unitary piece of molded material using techniques known in the art. Alternatively, the endoscopic hood is formed of separate interlocking pieces that are assembled and then irreversibly joined or fused by heating, gluing, soldering welding or the like. Whether formed as separate interlocking components, or as a single unitary piece, a wide range of materials may be used to make the endoscopic hood 10 and/or sleeve 22. Suitable materials may include metals, polymers, metal-polymer composites, and the like. Some examples of suitable metals and metal alloys include stainless steel, such as 304V, 304L, and 316LV stainless steel; mild steel; nickel-titanium alloy such as linear-elastic and/or super-elastic nitinol, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include Poly (methyl methacrylate) (PMMA), polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyam ides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenyleneterephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, polyisoprene, other suitable materials, or mixtures, combinations, copolymers thereof, polymer/metal composites, and the like. These are just examples and should not be seen as limiting.

The proximal portion 11 of the endoscopic hood 10 is dimensioned to receive the distal end of an endoscope (not shown). The endoscopic hood 10 may be designed to either permanently or temporarily attach to the distal portion of the endoscope by an attachment mechanism. Permanent attachment mechanisms may include gluing, welding, soldering or the like, while temporary locking mechanisms may include a snap-fit, screw-fit, luer-lock, press-fit using a silicone component or similar device formed into the endoscopic hood 10. In some instances, the endoscopic hood 10 may be integral to the to the endoscope shaft. In some instances, the cross-sectional shape of the proximal portion 11 may be substantially circular, though other shapes may be employed as necessary to receive the distal end of the endoscope (not shown). Inwardly projecting stops 17 are optionally included within the lumen 13 of the endoscopic hood 10 to provide a secure stopping point against which the distal end of the endoscope may be pressed in an interference fit.

The dimensions of the endoscopic hood 10 may vary according to a variety of factors, include the desired application and size of the patient. For example, an endoscopic hood designed for rectal insertion may be considerably smaller than an endoscopic hood designed for insertion into the esophagus. The endoscopic hood 10 may be designed for multiple or single uses. As a single-use device, for example, the endoscopic hood 10 may include temporary attachment mechanism and may be stored in hermetically sealed, sterile packaging before use. A multiple-use device, however, may be designed of materials able to withstand high temperature and high pressure sterilization conditions such as those provided by an autoclave.

The present disclosure is not limited to embodiments in which the resection wire 40 is secured at a first end 41 to an anchoring element 20 located on a distal portion 12 of the endoscopic hood 10. In one embodiment, the first end 41 of the resection wire 40 is not anchored to a distal portion 12 of the endoscopic hood 10, but instead travels proximally along an inner or outer portion of the endoscopic hood and rejoins the resection wire at a more central portion (not shown). In another embodiment, the first end 41 of the resection wire 40 is anchored to a proximal portion 11 of the endoscopic hood (not shown).

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

We claim:
1. A tissue resection system, comprising:
an endoscope having a distal end;
an endoscopic hood coupled to the distal end of the endoscope, the endoscopic hood comprising:
  a proximal portion;
  a distal portion;
  a lumen extending between the proximal and distal portions of the endoscopic hood;
  a resection wire track disposed about an inner circumference of the distal portion; and
  a resection wire channel extending between the proximal and the distal portions of the endoscopic hood, wherein the resection wire channel is in communication with the resection wire track and wherein the resection wire channel comprises a slot formed in a wall of the endoscopic hood, the slot following a helical path between the proximal and the distal portions of the endoscopic hood;
a resection wire received by the resection wire channel and the resection wire track, wherein the resection wire is configured to form a loop about the resection wire track and extend proximally from the loop along the slot of the resection wire channel; and
an actuation handle coupled to a proximal end of the resection wire, wherein actuation of the actuation handle is configured to move the resection wire along the resection wire track and the slot of the resection wire channel.

2. The tissue resection system of claim 1, wherein a portion of the resection wire loop at the resection wire track is configured to move from an open-loop configuration to a closed-loop configuration.

3. The tissue resection system of claim 2, wherein advancing the actuation handle moves the portion of the resection wire into the open-loop configuration.

4. The tissue resection system of claim 1, wherein the endoscopic hood includes an inner base, and an outer sleeve received about an outer surface of the inner base.

5. The tissue resection system of claim 4, wherein a groove is formed along the outer surface of the inner base, and the groove is covered by an inner surface of the outer sleeve to form the slot.

6. The tissue resection system of claim 1, wherein the distal portion of the endoscopic hood has a smaller diameter than the proximal portion of the endoscopic hood.

7. A tissue resection system, comprising:
an endoscope having a distal end;
an endoscopic hood coupled to the distal end of the endoscope, the endoscopic hood comprising:
  an inner base, including:
    a resection wire channel formed thereon, the resection wire channel having a proximal end and a distal end, the proximal end of the resection wire channel being circumferentially offset from the distal end of the resection wire channel, wherein the resection wire channel extends radially inwardly from a surface of the inner base, and wherein the surface faces radially outwardly, and
    a resection wire track at a distal end portion of the inner base; and
  an outer sleeve received circumferentially about the inner base; and
a resection wire received by the resection wire channel and the resection wire track, wherein the resection wire is configured to form a loop about the resection wire track and extend proximally from the loop along the resection wire channel; and
an actuation handle coupled to a proximal end of the resection wire, wherein actuation of the actuation handle is configured to move the resection wire along the resection wire track and the resection wire channel.

8. The tissue resection system of claim 7, wherein the outer sleeve covers a portion of the surface of the inner base that faces radially outwardly.

9. The tissue resection system of claim 8, wherein the outer sleeve covers the resection wire channel.

10. The tissue resection system of claim 7, wherein the inner base includes a rim at a distalmost end of the inner base, and wherein the rim has a recess formed therein for connecting the resection wire channel with the resection wire track.

11. The tissue resection system of claim 10, wherein the recess is a groove, and wherein the outer sleeve includes a radially inwardly extending flange that covers the groove.

12. A tissue resection system, comprising:
an endoscope having a distal end;
an endoscopic hood coupled to the distal end of the endoscope, the endoscopic hood comprising:
  a proximal end;
  a distal end;
  a radially outer surface;
  a protrusion protruding radially outwardly from the radially outer surface, wherein the protrusion is distal to the proximal end, and wherein the protrusion has a passage extending therethrough;
  a resection wire channel extending between the protrusion and the distal end; and
  a resection wire track at the distal end;
a resection wire received by the passage, the resection wire channel, and the resection wire track, wherein the resection wire is configured to form a loop within the resection wire track; and
an actuation handle coupled to a proximal end of the resection wire, wherein actuation of the actuation handle is configured to move the resection wire along the passage, the resection wire channel, and the resection wire track.

13. The tissue resection system of claim 12, wherein the endoscopic hood includes an inner base and an outer sleeve.

14. The tissue resection system of claim 13, wherein a proximal portion of the protrusion is part of the inner base, and a distal portion of the protrusion is part of the outer sleeve.

15. The tissue resection system of claim 14, wherein the proximal portion of the protrusion includes an aperture that receives the resection wire, and the distal portion of the protrusion covers the aperture.

16. The tissue resection system of claim 12, wherein the endoscopic hood has a central longitudinal axis, wherein a proximal end of the resection wire channel lies at a first position relative to the central longitudinal axis, wherein a distal end of the resection wire channel lies at a second position relative to the central longitudinal axis, and wherein the first and second positions are on opposite sides of the central longitudinal axis.

17. The tissue resection system of claim 16, wherein the resection wire channel follows a helical path between the first and second positions.

\* \* \* \* \*